United States Patent [19]

Smith

[11] Patent Number: 5,143,060
[45] Date of Patent: Sep. 1, 1992

[54] INSULATED CARBON DIOXIDE ABSORPTION SYSTEM

[76] Inventor: Charles A. Smith, 811 Starlite Dr., Louisville, Ky. 40207

[21] Appl. No.: 590,947

[22] Filed: Oct. 1, 1990

Related U.S. Application Data

[63] Continuation-in-part of Ser. No. 363,531, Jun. 8, 1989, abandoned.

[51] Int. Cl.⁵ .......................................... H61M 16/22
[52] U.S. Cl. .......................... 128/205.28; 128/204.17; 128/205.12; 138/121; 138/148
[58] Field of Search ............... 128/205.28, 205.27, 128/205.12, 204.17, 201.13, 911, 201.25, 201.27, 202.26, 203.26, 203.27; 138/109, 121, 122, 148, 149, 173; 285/47

[56] References Cited

U.S. PATENT DOCUMENTS

| | | | |
|---|---|---|---|
| 2,898,941 | 8/1959 | Kilcup | 138/121 |
| 3,088,810 | 5/1963 | Hay | 128/205.28 |
| 3,566,867 | 3/1971 | Dryden | 55/512 |
| 3,721,238 | 3/1973 | Wise et al. | 128/205.24 |
| 3,814,091 | 6/1974 | Henkin | 128/202.22 |
| 4,007,737 | 2/1977 | Paluch | 128/201.13 |
| 4,193,966 | 3/1980 | Dowgul | 128/205.28 |
| 4,463,755 | 8/1984 | Suzuki | 128/204.18 |
| 4,491,130 | 1/1985 | Pasternack | 128/201.13 |
| 4,548,730 | 10/1985 | Koslow | 128/202.26 |
| 4,576,616 | 3/1986 | Mottram et al. | 128/205.27 |
| 4,727,871 | 3/1988 | Smargiassi et al. | 128/205.27 |
| 4,822,572 | 4/1989 | van der Smissen et al. | 128/202.26 |

FOREIGN PATENT DOCUMENTS 0082246 6/1983 European Pat. Off. ....... 128/205.28

Primary Examiner—Edgar S. Burr
Assistant Examiner—Stephen R. Funk
Attorney, Agent, or Firm—Kinzer, Plyer, Dorn McEachran & Jambor

[57] ABSTRACT

A system for use with assisted human breathing systems which includes an enclosure adapted to receive a granular material for absorption of carbon dioxide from the air exhausted from a patient using the system. An exhausted air inlet is provided to the device, and a return air outlet is provided from the device to the user. The exhausted air inlet and the return air outlet are in communicative relation through the granular material contained within the apparatus. The enclosure which contains the granular material is insulated so that heat generated by the absorption of carbon dioxide onto the granular material is retained by the return air stream emitted from the enclosure. Insulated tubing can be provided to be connected between the device and the patient so as to decrease heat loss and condensation of moisture from the circulating air. The enclosure can isolate breathing gases from other parts of the system to prevent contaminated patient gases from contacting mechanical parts of an anesthesia machine associated with the breathing system, and prevent contamination of the patient by gases that have been in contact with internal mechanical parts of the anesthesia machine which have been in contact with gas breathed by prior patients.

11 Claims, 4 Drawing Sheets

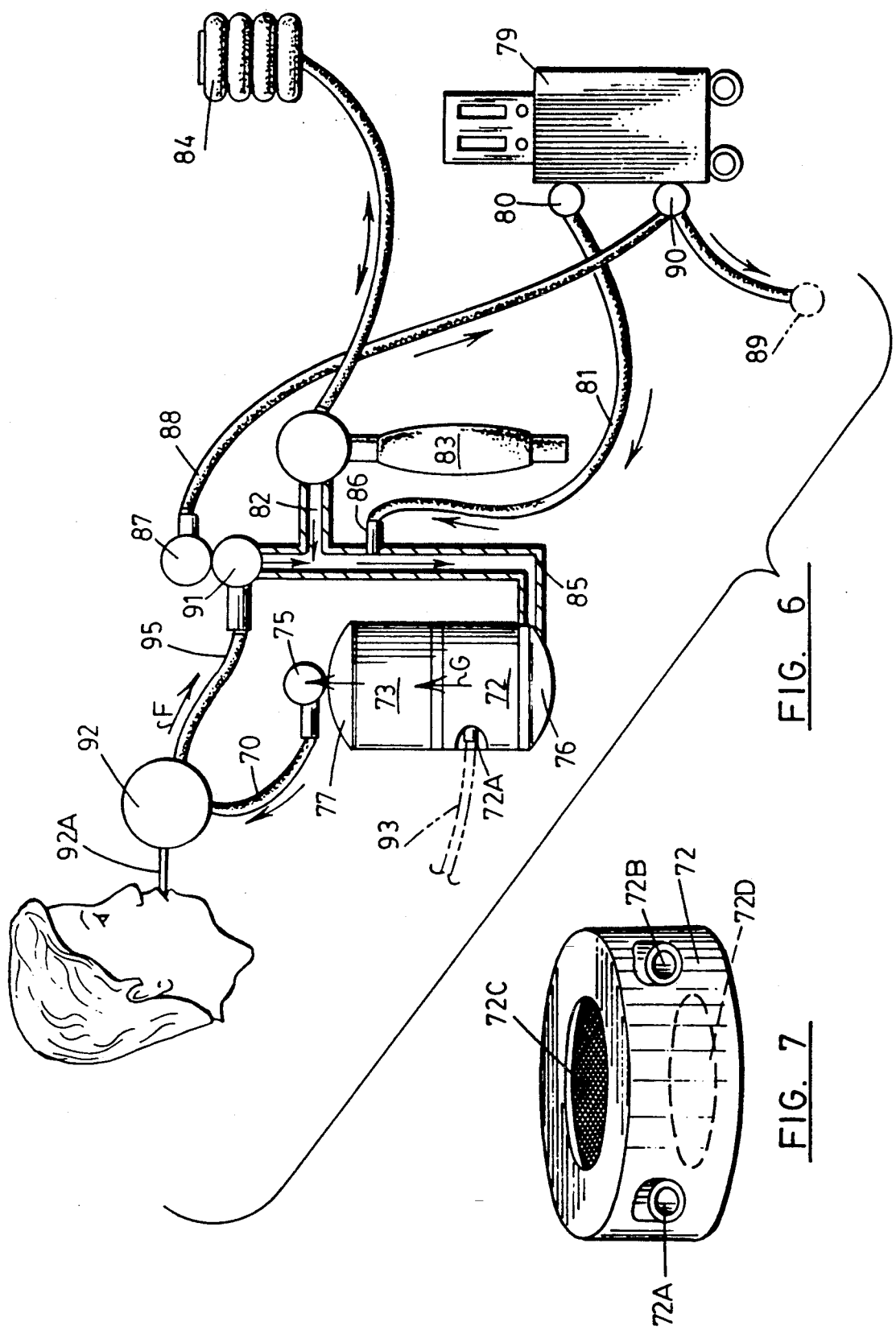

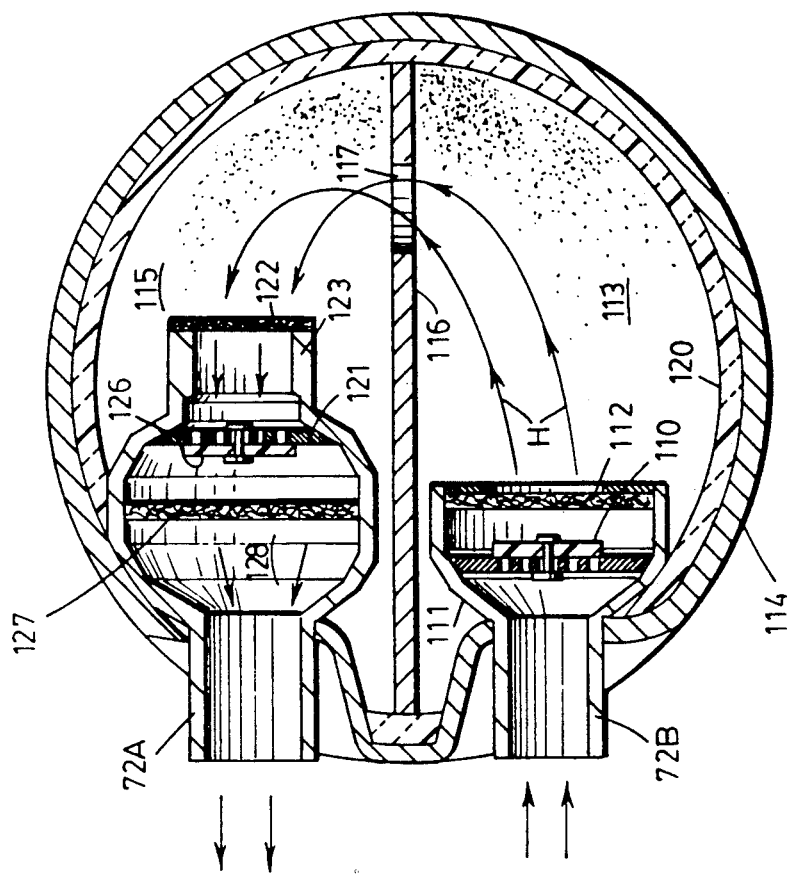
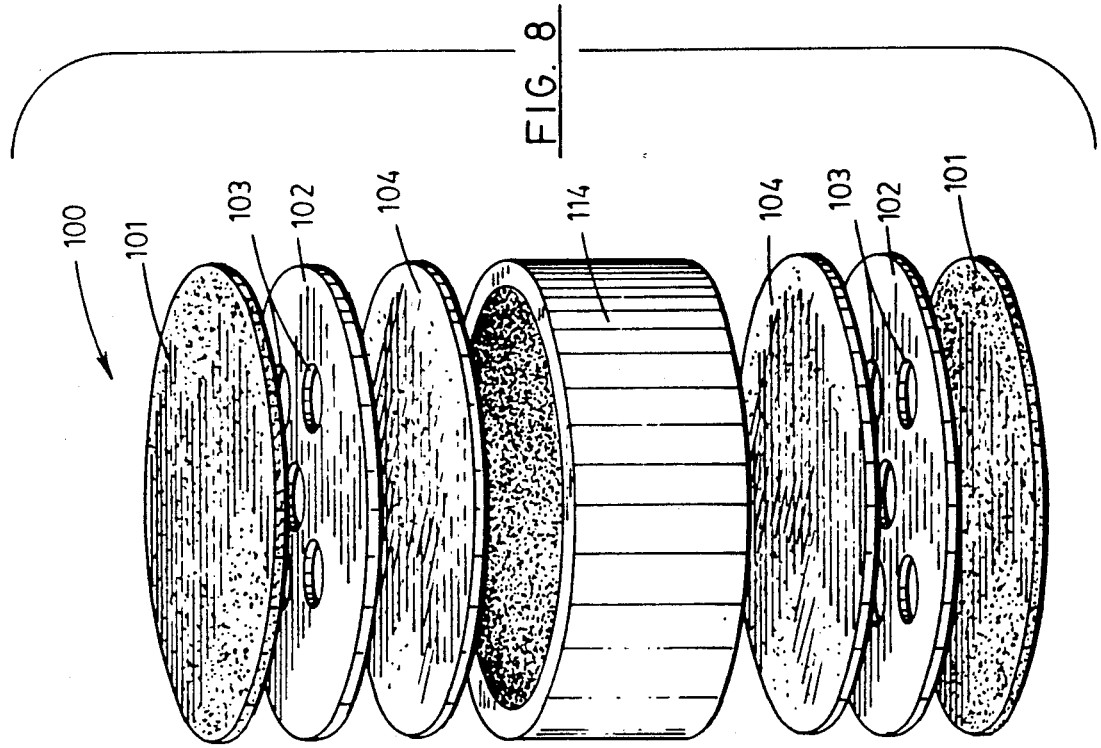

INSULATED CARBON DIOXIDE ABSORPTION SYSTEM

REFERENCE TO RELATED CASES

This application is a continuation-in-part of application Ser. No. 07/363,531, filed Jun. 8, 1989 now abandoned.

BACKGROUND OF THE INVENTION

Background Art

The present invention relates particularly to breathing assistance systems and more particularly to the type of breathing assistance systems found in surgical operating rooms, and similar medical applications.

In the use of such systems, particularly with patients who are experiencing breathing difficulty because of trauma, surgical procedures, or for other reasons, it is generally desirable to provide heated and humidified air to the patient to prevent "drying out" of the mucocilliary tissue of the respiratory system, and reduce patient heat loss caused by evaporation of water vapor from the lungs.

Heretofore, complicated, hazardous and expensive apparatus has been required to condition the air supplied to the patient. Where such a system is in use for a surgical procedure, or other operating room technique, anesthesia gases or other conditioning is often provided for the breathing gas stream. Also, in many applications, it is particularly useful and economical for the air to be recirculated. However, recirculation requires the removal of carbon dioxide from the gas exhaled by the patient.

Such prior art systems for warming and humidifying patient gases require the use of water reservoirs, humidifiers, and complicated delivery systems including complex electrical/electronic controls. Those systems further require complicated hose connections, and knowledge of the control systems; they may require a significant amount of space in the operating room. Setup of these prior art systems is complicated, and the prior art systems require substantial capital outlay as well as costly supplies.

In such previous applications the use of heaters and humidifiers is prevalent in order to provide proper conditioning for the gases supplied to the patient.

No prior art arrangement is known which recognizes that by proper utilization of the heat typically generated by the reaction of carbon dioxide with a granular absorbent material, and proper insulation, the typical expensive and often troublesome heated humidifier, water supply, reservoir, hose connection system, electronic monitoring and control, bulky mounting apparatus, and generally complicated arrangements required by the prior art can be much simplified or eliminated.

No prior art teaching recognizes that such a device can also be isolated from an associated anesthesia machine to prevent cross contamination between patients. The device is further required to warm, humidify and filter the air stream returning to the patient.

SUMMARY OF THE INVENTION

The present invention relates to methods and apparatus for the heating and humidification of air to be supplied to a patient which eliminates electrical/electronic humidifiers, heaters, and other related apparatus, previously listed and generally required by previous procedures, to properly condition the air before it returns to the patient. In general, devices within the scope of the present invention absorb $CO_2$ from recirculated anesthesia gases, and simultaneously warm and humidify the gases. The devices can also include means for removal of bacteria and/or virus from the gas flow and means for filtering out migratory absorbent dust.

Devices within the scope of the present invention can be used with anesthesia machines to prevent contamination of the anesthesia machine with bacteria virus from the patient and to eliminate the need to decontaminate the machine between procedures.

In accordance with one feature of the present invention it has been unexpectedly found that there is sufficient heat generated by the exothermic reaction characteristic of the absorption of carbon dioxide from a breathing air stream to eliminate the need for auxiliary heating if the system utilizing the procedure is properly insulated. Accordingly, the present invention uses insulation methods and procedures to eliminate the complicated and expensive apparatus required in previous respiratory gas conditioning systems. It has also been found that the system is thermally self regulating, in that as more exhaled air is circulated, the greater the quantity of heating/humidification required. The amount of heat generated in the exothermic reaction correspondingly increases because of the increased quantity of carbon dioxide produced by the patient.

It has been further found that the above objectives can be accomplished in an apparatus within the scope of the present invention which also allows the isolation of the gas reconditioning device from an associated anesthesia machine.

More particularly, the present invention provides a system for use with assisted human breathing systems which includes an enclosure adapted to receive a granular material for absorption of carbon dioxide from the air exhausted from the user to the system. An exhausted air inlet is provided to the device, and a return air outlet is provided from the device to the patient. The exhausted air inlet is provided to the device, and a return air outlet is provided from the device to the patient. The exhausted air inlet and the return air outlet are in communicative relation through the granular material contained within the enclosure. Flow direction regulating devices are located within the enclosure, which is insulated so that heat generated by the adsorption of carbon dioxide onto the granular material is retained by the return air stream emitted from the enclosure. Insulated tubing can be provided to be connected between the device and the user to decrease heat loss and condensation of moisture from the circulating air. The enclosure can isolate breathing gases from other parts of the absorber and prevent contaminated patient gases from contacting mechanical parts of an anesthesia machine associated with the breathing system.

Accordingly, the invention provides for a system for use in the assisted respiration of a patient during an anesthesia procedure, the system including an enclosure retaining a granular material for absorption of carbon dioxide from the air exhausted by the patient, an air inlet means and an air outlet means each in communication through said granular material, and a tubular respiration means including an insulation means, the insulation means surrounding the tubular respiration means along a substantial portion of its entire length.

The inventive device also provides for an insulated breathing conduit for use in a respiratory system, where the conduit provides an air stream communication between a user and an air purification and respiratory device, and where the conduit further comprises an inner wall member defining a tubular passage for air stream communication, an air impermeable, tubular, outer wall member having two oppositely disposed ends and surrounding the inner wall member, each end of the outer wall member sealingly engaging the inner wall member at each of its ends, the inner wall member and the outer wall member together defining a substantially annular space between the members having no air stream communication with the ambient environment, and including a means for connecting the conduit to the user and to other elements of the air purification and respiratory device.

Examples within the scope of the present invention are illustrated in the accompanying drawings and discussed hereinafter but it will be understood that other arrangements also within the scope of the present invention will occur to those skilled in the art upon consideration of the illustrations provided herewith and reviewing the discussion provided hereinafter.

BRIEF DESCRIPTION OF THE DRAWINGS

Examples in accordance with the present invention are illustrated in the accompanying drawings wherein:

FIG. 4A is a view taken along a plane passing through line 4—4 of FIG. 3;

FIG. 4B is a view taken along a plane passing through line 5—5 of FIG. 3;

FIG. 5 is a perspective view of an example of the canister of FIG. 2;

FIG. 6 is a flow schematic of an apparatus within the scope of the present invention in a breathing circuit with an anesthesia machine;

FIG. 7 is a perspective view of another example of an apparatus in accordance with the present invention for use in an application as shown in FIG. 6;

FIG. 8 is an exploded perspective view of several of the elements of a device within the scope of the present invention; and FIG. 9 is a cross-sectional plan view of a device similar to the one shown in FIG. 7.

DETAILED DESCRIPTION OF THE DRAWINGS

Figure 1:
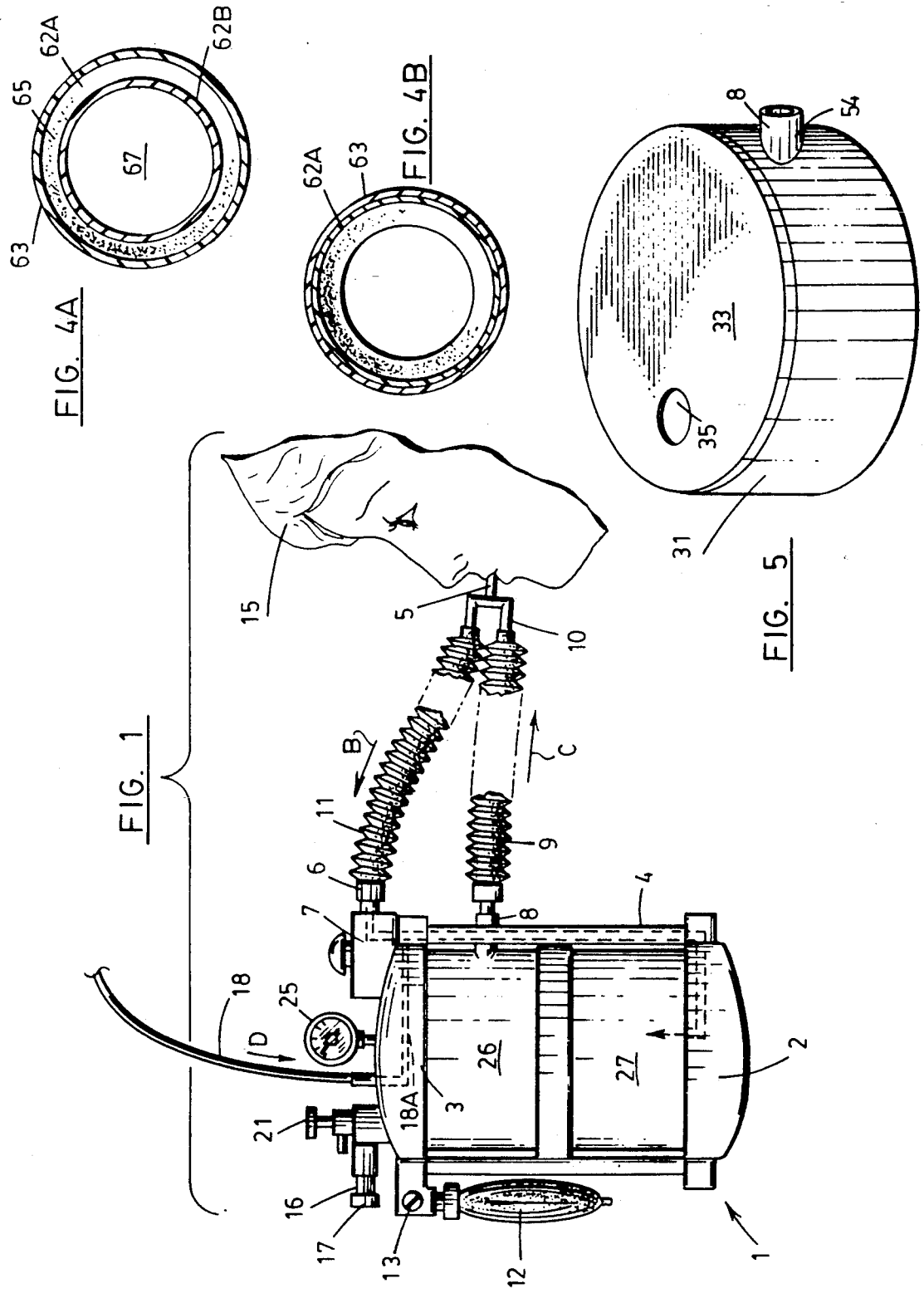
FIG. 1 is an overall elevation view of a system within the scope of the present invention.

Referring first to FIG. 1, a breathing system within the scope of the present invention is shown which provides overall heat and moisture balance in a manner to eliminate the need for electrical or other evaporation or auxiliary air heating equipment. As previously stated, one problem encountered in connection with various medical procedures in an operating room is the maintenance of a warm and moist air supply to the patient undergoing anesthesia. It is well known that the maintenance of an air supply including moisture and warmth, is of particular importance if unplanned hypothermia is to be avoided.

In FIG. 1, a patient 15 is shown receiving a "Y" tube 10 with an outlet 5 to supply air to the patient and for return of air to the breathing system. In a typical breathing system return air exhaled by the patient, shown by arrow B, is supplied to a carbon dioxide absorbent device for the removal of carbon dioxide and adjustment of anesthesia concentration, where necessary. Purified air is returned to the patient as shown by arrow C. In the arrangement shown, a receptacle 1 is provided having a top member 3 and a bottom member 2. Receptacle 1 is adapted to receive an absorbent canister 26 between members 2 and 3 so that air recirculated from the patient through a hose or tube 11 to an inlet 6 is passed downwardly through a conduit 4 and, as shown, through a cooperative conduit in the bottom member 2, to pass upwardly into a first chamber 27 and then to a second chamber in canister 26.

In a typical apparatus, the air is supplied to the patient through an outlet 16. However, an outlet 16 is not required in devices within the scope of the present invention because an outlet 8 is provided from the canister 26 for return of filtered, conditioned air as is described below. As also shown in FIG. 1, a cap 17 can be provided over the outlet 16 which is normally used for return air to the patient.

Typically, in arrangements of the type shown in FIG. 1, where devices within the scope of the present invention will be utilized as shown in FIG. 1, an air bag 12 can be provided to supply air to the patient where assisted respiration is required.

Also, a fresh gas line 18 can be provided to the device for the addition of anesthesia gases as required. As is known in the art, an internal conduit 18A can be provided to supply fresh gas, which flows in the direction indicated by arrow D, to conduit 4.

A pressure release valve 21 and pressure indicating gauge 25 are also present to prevent excessive pressure in the system which could injure the patient.

It has been found that in devices in accordance with the present invention, insulation of air conduits 9 and 11, as described hereinafter, is particularly useful in connection with operation of the devices. In prior apparatus, where noninsulated air conduits are utilized, condensation occurs in the hoses, particularly in the exhalation or return air conduit 11, but also in the inhalation or supply conduit 9. When an electrical heater/humidifier is used, condensation occurs even more in the supply conduit 9. Use of insulated conduits is described below and is also described in more detail in a copending U.S. patent application Ser. No. 275,940, directed to devices in which condensation is virtually eliminated. Devices according to the invention described in the copending application, in conjunction with the use of an absorbent canister within the scope of the present invention eliminates the need for complicated, expensive auxiliary humidifiers and heaters which are required in the prior art.

Figure 3:
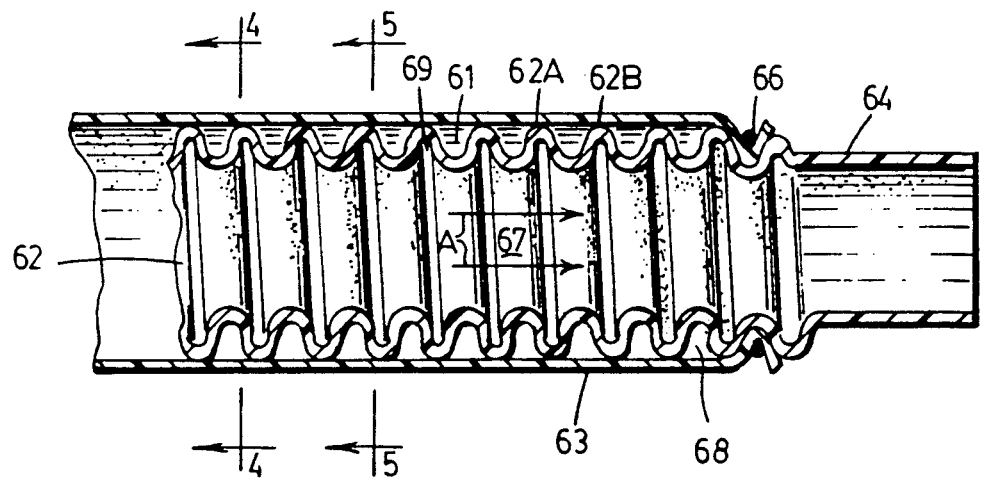
FIG. 3 is a cross-sectional view of a breathing tube useful in the systems in accordance with the present invention.

With reference to the conduits 9 and 11 of FIG. 1, FIG. 3 illustrates a breathing tube which is useful in devices of the type contemplated by the present invention.

A corrugated tube 62 of the type generally known in the art is provided and a casing 63 is provided, as described hereinafter, to encase the tube 62 to define an insulating dead air space 61 between the breathing tube 62 and the casing 63. A tip 64 is provided at the end of the tube 62 to facilitate connection of the tube either to a source of gas or to a mouthpiece or other device to be received by a patient. As is known in the art, a similar arrangement can be provided on the other end of the tube and the tube is utilized to supply gases from a source to the patient and to return exhaled gases to the source. As is also known in the art, corrugations 62A, 62B are provided along the length of the tube 62 to facilitate bending or shaping the tube to a selected configuration conducive to use by the patient.

The casing 63 can be retained on the tube 62 by any convenient means and in the arrangement shown an elastomeric fastener, for example a rubberband 66, or "O" ring is provided to be placed over the outer surface of the casing 63 and is received between the raised portions of the tubing to hold the casing under the rubberband 66 in one of the valleys between the corrugations.

There are several features which should be considered in connection with the arrangement shown in FIG. 3. The first is that the air represented by the arrows A flows through the opening 67 in the tube and contacts principally the lower portions 62B of the corrugations. As is known in the art, the heat transfer occurring in the tube occurs in the area of highest Reynolds number. Since the Reynolds number is dependent on velocity, the highest heat transfer will occur in the areas 62B on the inner surface of the corrugations. Conversely, the air trapped in the depression 69 is generally stagnant compared with the air flowing through the opening 67. Since the stagnant air provides some insulation within the tube, less heat transfer occurs through the area 69 in the upstanding portions of the corrugations. In practice, without the use of the casing 63, heat is transferred through the areas 68 of the corrugated tubing and convective currents flowing through the areas 61 facilitate loss of heat through the areas 68 to the ambient air surrounding the tube 62.

It is recognized that the device according to the present invention effectively eliminates these convective currents so the heat loss which would otherwise occur through the areas 68 of the corrugated tubing is substantially reduced. Further, the casing 63 can have a wall thickness less than the thickness of the corrugated tubing wall to maintain flexibility of the entire unit yet because of the lack of corrugations 62A, 62B, which directly contact the ambient environment, the casing 63 substantially reduces the surface area available for convective heat transfer. Additionally, the casing 63 provides another barrier for radiant heat loss as well as preventing contact of the corrugated tubing with ambient air.

Casing 63 can be clear, as is the corrugated tubing 62, so that the presence of condensate in the tube can be monitored visually. Additionally, the overall length of the casing 63 is less than the extended length of the corrugated tubing 62 so that the surface area of the casing is substantially less than the surface area of the corrugated tubing to further reduce heat transfer.

Accordingly, the arrangement in FIG. 3 permits the transmission of a stream of air through a relatively long tube with virtually no change in temperature and with very little additional expense, bulk, or loss of flexibility or loss of visual contact with tube 62.

Figure 2:
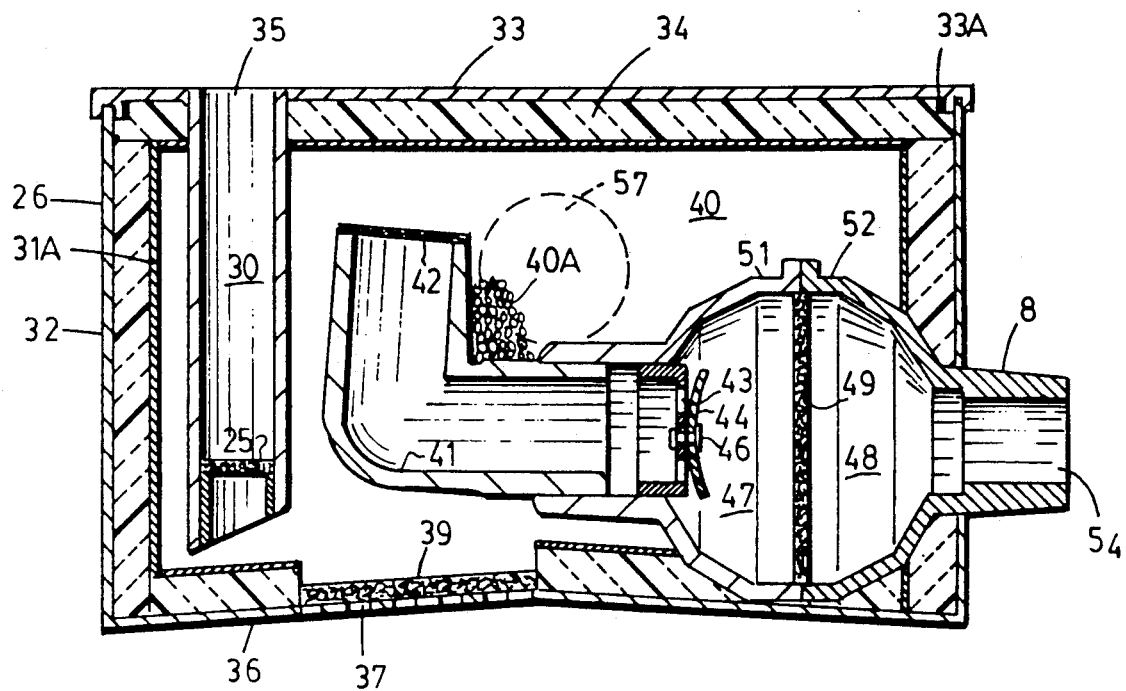
FIG. 2 is a cross-sectional elevation view of an example of a canister device within the scope of the present invention for use with breathing systems.

FIG. 2 is an illustration in cross section of an example of a canister 26 shown in FIG. 1 within the scope of the present invention. FIG. 2 shows chamber 40 defined by an outer enclosure 32 and filled with a granular absorbent 40A.

The outer enclosure 32, for example a tubular enclosure, is provided with a lid 33 for the canister 26. A seal 33A can be located around the edge thereof to prevent the escape of air.

The walls 32 and 33 are insulated by means of insulation 31 and 34, for example expanded polyethylene materials. As shown, a reflective film 31A can be provided on insulation 31, 34 to prevent loss of radiant heat. Also, an opening 57 can be provided to allow visual observation of absorbent 40A located in the chamber 40. While expanded polyethylene materials are utilized in the example shown, it will be understood that other insulating materials can also be utilized within the scope of the present invention.

As shown, a vent tube 30 can be disposed within chamber 40 and attached to the lid 33. An outer opening 35 provides access through the lid 33 for the vent tube 30. A barrier 25 can be positioned to prevent passage of absorbent material 40A out of the chamber 40 of the device. A bottom wall 36 is provided which, as shown, can be slightly concave with an apertured section 37 to provide an air inlet for the return of air to the absorbent material located within the canister 26 which forms the chamber 40. Apertured section 37 is typically in communication with the chamber 27, shown in FIG. 1.

An air-pervious barrier material 39 can be provided on the inside of the apertured section 37 to prevent escape of absorbent material 40A, as well as dust from the material, both of which are located in chamber 40.

Air flows through the absorbent material 40A in the chamber 40 and is then passed through an inlet barrier 42, which prevents passage of dust or granular material from chamber 40 to an outlet filter assembly by means of an upturned elbow 41 which is disposed in the outlet filter assembly, described hereinafter.

Barrier 42 allows the admission of air without admission of dust or particles of the absorbent material for recirculation of the air to the patient after removal of carbon dioxide from the air stream.

The elbow 41 is received in a filter chamber comprising two mating segments 51 and 52 having a bacteria/virus filter barrier 49 located across the filter chamber. The filter barrier 49, as is known in the art, removes bacteria and some viruses which may have been introduced to the air stream as exhaled by the patient, or elsewhere, and allows the same canister 26 to be used for several patients in succession. Repeated use by different patients is possible because bacteria which may have accumulated in the canister 26 cannot be passed to successive patients.

An inlet chamber 47 and an outlet chamber 48 are defined on opposite sides of the filter barrier 49. As shown, the outlet of elbow 41 can be provided with a "check valve" type arrangement where the outlet of the elbow 41 has apertures 43. A pin 46 is provided toward the center of the outlet disc and adapted to retain a flexible flapper 44 so that air is allowed to pass into chamber 47 from the elbow 41. In the event the pressure at the chamber 47 exceeds the pressure in the elbow 41, however, the flapper 44 closes against the apertures 43 to prevent back flow.

The outlet 8 from the filter outlet chamber 48 is connected to the recycle conduit 9, as is shown in FIG. 1.

In summary, it has been unexpectedly found that devices within the scope of the present invention normally eliminate the need for heating or moisturization of the air supply to a patient during an operating procedure, thus substantially eliminating the risk involved with such ventilation procedures and greatly reducing the cost incurred in providing such services. In virtually all testing cases, it has been found that more than adequate heat is produced by the chemical reaction occurring in the absorption of the $CO_2$ onto the absorbent material 40A, for example soda lime. It is further recognized that devices within the scope of the present invention are self regulating, in that the amount of heat generated is directly proportional to the rate of breathing and to the air flow containing $CO_2$ which, in turn, determines the amount of heat and water vapor. By the use of the insulated conduits previously described and the use of the insulated canister previously described it has been found that a self-sustaining heating and humidification system can be provided.

FIG. 6 is a schematic illustration showing another mode of operation of devices within the scope of the present invention with slight modification of the filter of the adsorpter.

In FIG. 6, an anesthesia circuit is shown where an anesthesia machine 79 is provided to supply anesthesia at a controlled rate from an outlet 80, through a tube 81, to an inlet 86 of a manifold 85. Manifold 85 includes an inlet valve 91 to receive recycled air, shown by arrow F, from the patient. Manifold 85 further includes an inlet 82 which is provided for air flow from a breathing assist bag 84, having a balloon 83 to equalize fluctuations in pressure. A release valve 87 is provided adjacent the inlet valve 91 to prevent over pressure by supplying air to a scavenger valve 90 connected to an air reject system 89 (shown in phantom) as also known in the art.

In the arrangement shown in FIG. 6, air from the manifold 85 is supplied to an absorber chamber 76 on the lower portion of an absorber assembly. Canisters 72, 73 within the scope of the present invention as described hereinafter are located in the assembly. In the arrangement shown, an outlet 72A can be provided from the absorber canister 72 to supply air through a conduit 93 (shown in phantom) to the patient. Alternatively, the outlet 72A can be capped to allow air flow, as indicated by arrow G, to proceed upwardly through openings in the bottom of the canister 72, the bottom of a canister 73, and out through an outlet valve 75 in the top 77 of the assembly. The air then proceeds by means of a conduit 70 to the patient. The arrangement shown allows the complete isolation of the air from the patient to prevent contamination of either the anesthesia machine or any other associated equipment, contrary to prior art arrangements.

In the arrangements shown, the air is conducted from the patient by means of a conduit 95, for example the isolated conduit previously described herein, to the manifold 85, where anesthesia is added if necessary. Also, means are provided for assistance of breathing if necessary. The air then proceeds to the absorber chamber 72 where the $CO_2$ is removed, thus heating the granular material within the chamber and revaporizing a portion of the liquid in the chamber to humidify the air which is then emitted through the outlet 72A or through the outlet 75 of the absorber device through the conduit 70 to a "Y" tube 92 and an outlet 92A directing to the patient as in the embodiment of FIG. 1.

FIG. 7 is a perspective view of an example of an absorber canister 72, 73 of the type which would normally be used in devices as shown in FIG. 6.

In FIG. 7, a canister 72 is provided (to hold granular material as described hereinafter) where top inlet 72C and bottom inlet 72D are provided and are suitably barriered for filtration of air, as also described hereinafter. Alternatively, an inlet 72B and an outlet 72A are provided for when the canister 72 is to be used without utilization of the top and bottom inlet and outlet, 72D and 72C respectively.

Turning now to FIG. 8, which is an exploded perspective of the barrier arrangements utilized in the device and the type shown in FIGS. 6 and 7, both the inlet and the outlet are provided with a filtration device, generally indicated at 100. The filtration device 100 includes a sandwich in which a bacteria filter 101 is provided on the outermost edge of both the inlet and outlet. The bacteria filter 101 removes bacteria or viro which may be present in the air stream and prevents the passage of the bacteria either back to the patient or likewise into the anesthesia machine or other equipment.

The bacteria filter 101 is then backed up by a support 102, which includes apertures 103 to allow flow of air through the support 102, but to prevent compression of either the filter 101 or a barrier 104 to the point that air flow is prohibited. Barrier 104 is provided to prevent the migration or escape of the soda lime dust or particles generated within the adsorber device 100 by the movement of the granules or the dust which is normally present on any granular material.

FIG. 9 is a cross section planar view of a typical arrangement of the type shown in FIG. 6 illustrating air flow through the device utilizing the inlet 72B and the outlet 72A. The air flow is shown in general by the arrows H, and an inlet assembly 111 is provided having a one-way valve 110 of the type previously described to prevent back flow of air and soda lime. The inlet assembly 111 includes a barrier 112, as also previously described, to prevent migration of dust particles from the soda lime retained within the chamber 113, which is defined partly by the enclosure 114.

An air impervious separator 116 is located diametrically across the chamber 113 and defines another wall portion of the chamber. An aperture 117 is provided in the separator 116 to allow flow of air from the chamber 113 to chamber 115, which is defined on the opposite side of the barrier 116 by enclosure 114. As also shown, insulation 120 is provided around the internal surface of enclosure 114 defining chambers 113 and 115 to prevent heat lost and to facilitate rewarming and rehumidification of air passing through the device. The soda lime disposed within the chambers 113 and 115 and the barrier 116 is provided, of course, to extend the flow path of the air flow through the device so as to facilitate a greater degree of contact of air with the soda lime for $CO_2$ adsorption.

Chamber 115 further includes an outlet assembly 121, which is similar to the assembly shown in FIG. 2. Outlet assembly 121 has a soda lime barrier 122 covering an inlet 123 to the device. A one-way valve 126 is provided to limit air flow in the direction shown by the arrows H and a bacteria/virus filter 127 is located across the chamber 128 defined within the device. The air is then emitted through the outlet 72A to the patient, as also previously described. It will be understood that in the arrangements shown in FIGS. 7 and 9, the appropriate inlets and outlets can be covered to facilitate the use of the device either with or without the use of an anesthesia machine.

It will be understood that the foregoing are but a few examples of arrangements within the scope of the present invention and that other arrangements also within the scope of the present invention will occur to those skilled in the art upon reading the disclosure set forth hereinabove .

The invention claimed is:

1. A system for use with recirculation type breathing systems for conditioning air to be supplied to a patient including: conduit means from the patient to the system; enclosure means including a wall surrounding and retaining a bed of granular material for absorption of carbon dioxide from air exhausted from the patient through the conduit means; exhausted air inlet means to said enclosure means and return air outlet means from said enclosure means, where said exhausted air inlet means and return air outlet means are in communicative relation through said bed of granular material in said enclosure means; insulating means disposed adjacent and inside the wall of the enclosure means so that heat which is generated by adsorption of carbon dioxide onto said granular material is retained within said enclosure means and transferred to a return air stream emitted from said enclosure means; and a return conduit means in communicative relation between the return air outlet means and the patient for returning the return air stream to the patient.

2. The invention of claim 1 including insulated tubing provided to be connected between the enclosure means and said patient to decrease heat loss and condensation of moisture from circulating air.

3. A system for use in the assisted respiration of a patient during an anesthesia procedure, the system including an enclosure having a wall with an inner surface, the enclosure retaining a granular material for absorption of carbon dioxide from the air exhausted by the patient, an air inlet means and an air outlet means each in communication through said granular material in said enclosure, a first insulation means disposed between said enclosure wall inner surface and said granular material, and a tubular respiration means including a second insulation means, the second insulation means surrounding the tubular respiration means along a substantial portion of its entire length.

4. The system according to claim 3 wherein the tubular respiration means further comprises a tubular inner wall defining a tubular air passage and the insulation means comprises a tubular outer wall surrounding the inner wall substantially along the entire length of the tubular air passage, the inner wall having two ends and being in sealing relationship to the outer wall at each of the ends, the inner and outer walls effectively isolating a dead air space between the inner and outer walls.

5. A system for use in the assisted respiration of a patient comprising:
   a) an enclosure for retaining a granular material, the granular material having a carbon dioxide absorbing capability, the enclosure including an inside wall surface;
   b) an air inlet means in the enclosure for providing air stream communication into the enclosure;
   c) a first tubular respiration conduit for providing an air stream passage from the patient to the air inlet means;
   d) an air outflow means in the enclosure for providing air stream communication out of the enclosure;
   e) a second tubular respiration conduit for providing an air stream passage from the air outflow means to return air to the patient; and
   f) insulation covering essentially the entire area of the inside wall surface of the enclosure, whereby a patient's respiration exhaust air passes through the first tubular respiratory conduit and air inlet means, into the enclosure, the carbon dioxide in the exhaust air being absorbed by the granular material in the enclosure, the air then passing through the air outflow means and the second tubular respiratory conduit to return to the patient, and whereby exothermic absorption of the carbon dioxide by the granular material generating heat, which heat is retained within the enclosure by the insulation covering the inside wall surface of the enclosure.

6. The system according to claim 5 wherein the first and second tubular respiratory conduits each comprise:
   a) an inner wall member defining a tubular passage for air stream communication;
   b) an air impermeable, tubular, outer wall member having a two oppositely disposed ends and surrounding the inner wall member, each end of said outer wall member sealingly engaging the inner wall member only at each of its ends, the inner wall member and the outer wall member together defining a substantially annular space between the wall members, the space being substantially isolated and having no air stream communication with the ambient environment; and
   c) means for connecting the conduit to the user and to other elements of the assisted respiration system.

7. The system according to claim 5 wherein the enclosure further comprises a barrier to the air stream including a means for the air stream to pass through the barrier, the means being disposed on the barrier, for diverting the air stream along a roundabout path through a major portion of the granular material within the enclosure.

8. The system according to claim 7 wherein at least one of the air inlet means or the air outlet means includes a flapper valve for ensuring a unidirectional flow of air through said enclosure.

9. The system according to claim 7 wherein the means for the air stream to pass through the barrier comprises at least one aperture disposed on the barrier at a distance from each of the air inlet and the air outlet means.

10. The system according to claim 5 wherein at least one of the air inlet means or the air outlet means includes a flapper valve for ensuring a unidirectional flow of air through said enclosure.

11. The system according to claim 5 wherein the air inlet means and the air outlet means each further comprise a barrier to allow for transmission of air, but not to allow transmission of dust or particles of the granular material within the enclosure.

* * * * *